(12) United States Patent
Zifeng et al.

(10) Patent No.: US 8,216,127 B2
(45) Date of Patent: Jul. 10, 2012

(54) ENDOSCOPE AND A METHOD OF MANUFACTURING THE SAME

(75) Inventors: Zhang Zifeng, Shenzhen (CN); Wang Zhenbo, Shenzhen (CN); Jiang Feng, Shenzhen (CN); Wang Kun, Shenzhen (CN); Huang Zhixue, Shenzhen (CN)

(73) Assignee: BYD Company Ltd., Shenzhen (CN)

( * ) Notice: Subject to any disclaimer, the term of this patent is extended or adjusted under 35 U.S.C. 154(b) by 706 days.

(21) Appl. No.: 12/346,745

(22) Filed: Dec. 30, 2008

(65) Prior Publication Data

US 2010/0022831 A1    Jan. 28, 2010

(30) Foreign Application Priority Data

Jul. 22, 2008   (CN) .......................... 2008 1 0068591
Jul. 25, 2008   (CN) .......................... 2008 2 0095923 U
Jul. 31, 2008   (CN) .......................... 2008 1 0142226

(51) Int. Cl.
    *A61B 1/04* (2006.01)
(52) U.S. Cl. .......................... 600/112; 600/109; 600/110
(58) Field of Classification Search .................. 600/109, 600/128, 129, 140, 110, 112
    See application file for complete search history.

(56) References Cited

U.S. PATENT DOCUMENTS

| | | | |
|---|---|---|---|
| 4,087,152 A | 5/1978 | Kolm | 339/252 R |
| 5,013,264 A * | 5/1991 | Tondreault | 439/636 |
| 5,021,888 A * | 6/1991 | Kondou et al. | 348/76 |
| 5,203,813 A | 4/1993 | Fitzsimmons et al. | 29/876 |
| 5,754,313 A * | 5/1998 | Pelchy et al. | 358/473 |
| 5,782,655 A * | 7/1998 | Stefaniu et al. | 439/510 |
| 5,873,816 A * | 2/1999 | Kagawa et al. | 600/134 |
| 5,879,285 A * | 3/1999 | Ishii | 600/110 |
| 6,142,930 A * | 11/2000 | Ito et al. | 600/109 |
| 6,567,115 B1 * | 5/2003 | Miyashita et al. | 348/76 |
| 6,945,929 B2 * | 9/2005 | Ando | 600/111 |
| 7,347,746 B1 | 3/2008 | He | 439/843 |
| 2004/0263680 A1 * | 12/2004 | Sonnenschein et al. | 348/375 |
| 2006/0109368 A1 * | 5/2006 | Ayrenschmalz | 348/340 |
| 2007/0182842 A1 * | 8/2007 | Sonnenschein et al. | 348/340 |
| 2007/0269996 A1 * | 11/2007 | Chia | 439/66 |
| 2009/0021618 A1 * | 1/2009 | Schwarz et al. | 348/294 |

* cited by examiner

*Primary Examiner* — Philip R Smith
*Assistant Examiner* — William Chou
(74) *Attorney, Agent, or Firm* — Morgan, Lewis & Bockius LLP (57) ABSTRACT

The present invention is directed to an endoscope that comprises a telescope, an imaging means, an image sensor for converting optical images produced by the imaging means to electrical signals, and a circuit board for receiving and outputting the electrical signals, the imaging means, image sensor and circuit board being located in the telescope. In some embodiments, the endoscope includes a connector that electrically connects the image sensor and the circuit board to form a first assembly.

19 Claims, 6 Drawing Sheets

ENDOSCOPE AND A METHOD OF MANUFACTURING THE SAME

RELATED APPLICATIONS

This application claims priority to Chinese Patent Application No. 200810142226.X, "An endoscope and a manufacturing method of the same," filed on Jul. 31, 2008, which is hereby incorporated by reference in its entirety.

This application claims priority to Chinese Patent Application No. 200810068591.0, "An endoscope and a manufacturing method of the same," filed on Jul. 22, 2008, which is hereby incorporated by reference in its entirety.

This application claims priority to Chinese Patent Application No. 200820095923.X, "A connector and an endoscope comprises the same," filed on Jul. 25, 2008, which is hereby incorporated by reference in its entirety.

This application relates to U.S. patent application, "A connector and a method of manufacturing the same," filed on Dec. 30, 2008 Ser. No. 12/346,753, which is hereby incorporated by reference in its entirety.

FIELD OF THE INVENTION

The invention relates to an endoscope, a method of manufacturing the same, and a connector for use in the endoscope.

BACKGROUND OF THE INVENTION

A traditional hard-telescope endoscope includes an object lens system, a turning lens system, an eyepiece lens system, and a telescope. Optical images transmitted from the object lens system can be displayed on a display after being processed by an optical system, which is usually located at the front telescope of the endoscope. Due to the long optical transmission distance of an optical image, this type of endoscope provides poor quality images.

To shorten the transmission distance of optical images and improve the image quality, there is a prior art electrical endoscope comprising an object lens, a charge coupled device (CCD) image sensor, a flexible circuit board, a telescope, and an operation system. According to the electrical endoscope, the optical signals from the object lens are converted to electrical signals by the CCD image sensor in the telescope, and processed to be displayed on the display. This endoscope can avoid the signal loss caused by the long distance of optical signal transmission and provide better quality images. But in order to position the object lens, CCD image sensor and multiple flexible circuit boards accurately, it is necessary to fill the telescope with adhesive and employ multiple connectors, resulting in a complicated structure and high manufacturing cost.

SUMMARY OF THE INVENTION

One purpose of the present invention is to provide an endoscope with simple structure and high image quality. Another purpose of the invention is to provide a method of manufacturing the endoscope of high image quality. Another purpose of the invention is to provide a connector for use in the endoscope.

According to some embodiments of the present invention, an endoscope comprises a telescope, an imaging means, an image sensor for converting optical images produced by the imaging means to electrical signals, and a circuit board for receiving and outputting the electrical signals, the imaging means, image sensor and circuit board being located in the telescope. The endoscope includes a connector that is configured to electrically connect the image sensor and the circuit board to form a first assembly.

According to some embodiments of the present invention, an endoscope comprises a telescope, an imaging means, an image sensor for converting optical images produced by the imaging means to electrical signals, and a circuit board for receiving and outputting the electrical signals, the imaging means, image sensor and circuit board being located in the telescope. The endoscope includes a holder located within the telescope. One end of the holder connects to the output end of the imaging means to form a first assembly and the other end of the holder is used to locate the image sensor.

According to some embodiments of the present invention, a method for manufacturing the aforementioned endoscope includes: using the connector to electrically connect the image sensor and the circuit board to form the first assembly; focusing the imaging means and the first assembly; and fixing them within the telescope.

According to some embodiments of the present invention, a connector comprises an insulation body and one or more conductive terminals set within the insulation body, each terminal including a head portion and a foot portion. A top surface of the head portion extends out of the end face of the body to form an engagement face. The foot portion extends from the head portion to form a bent end out of the other end face of the body. Multiple extension portions are formed by inclining outward the foot portion to tightly connect the terminal and the body.

BRIEF DESCRIPTION OF THE DRAWINGS

The aforementioned features and advantages of the invention as well as additional features and advantages thereof will be more clearly understood hereinafter as a result of a detailed description of embodiments when taken in conjunction with the drawings.

Like reference numerals refer to corresponding parts throughout the multiple views of the drawings.

DETAILED DESCRIPTION OF THE INVENTION

Reference will now be made in detail to embodiments, examples of which are illustrated in the accompanying drawings. In the following detailed description, numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Figure 1:
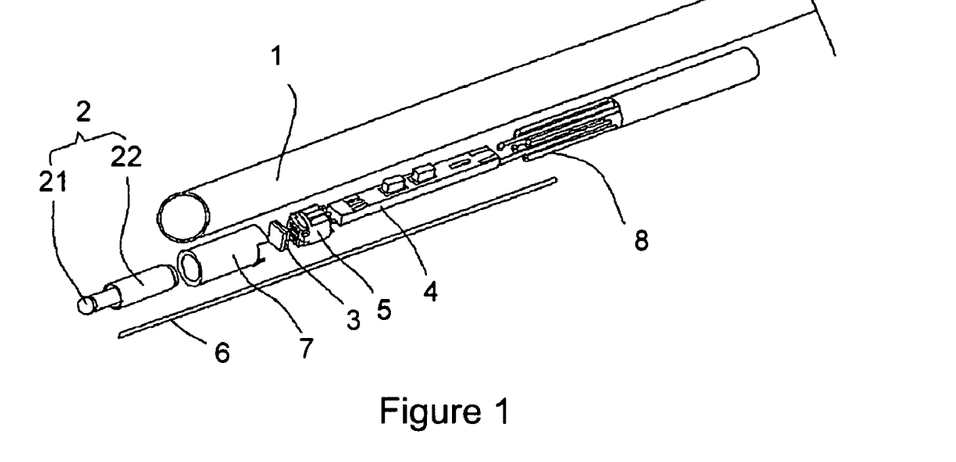
FIG. 1 is an exploded view of an endoscope according to one embodiment of the present invention.
Figure 2:
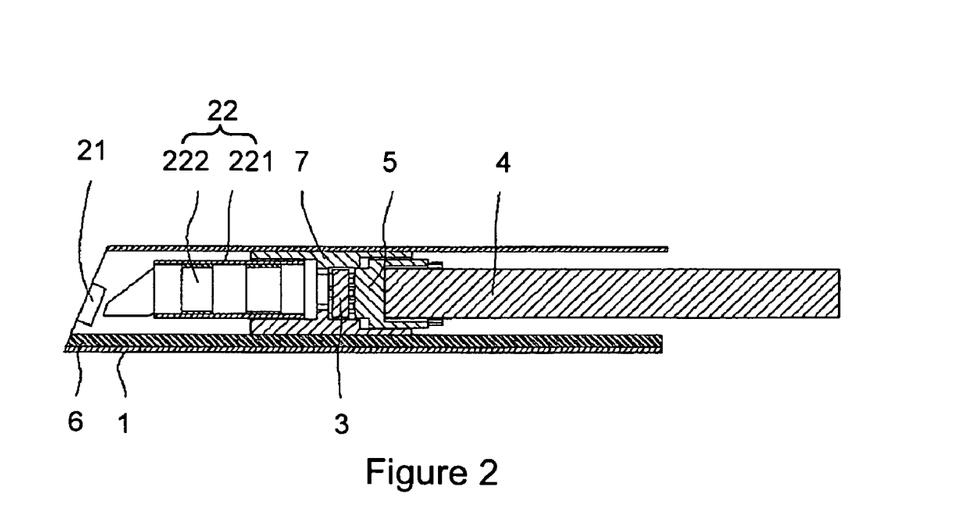
FIG. 2 is a cross-sectional view of the endoscope shown in FIG. 1.

FIGS. 1 and 2 illustrate an exemplary endoscope according to some embodiments of the present invention. The endoscope includes a telescope 1, an imaging means 2, an image sensor such as a CCD image sensor 3 that converts the optical signals of the imaging means 2 into electronic signals and a circuit board 4 that receives and outputs the electronic signals. The imaging means 2, image sensor 3 and the circuit board 4 are located in the telescope 1. The endoscope includes a connector 5 that connects the image sensor 3 and the circuit board 4 to form a first assembly. The connector 5 is configured to position the image sensor 3 and the circuit board 4 and transfer the electrical signals input from the image sensor 3 to the circuit board 4 to shorten the transmission distance of the signals and reduce the signal loss during the long transmission distance. As such, an endoscope according to the present invention can provide high quality images without the need for more connection parts.

The imaging means 2 is located at the front end of the telescope 1 and includes a lens 21 and a lens group 22. The output end of the imaging means 2 is coupled to one end of the optical fiber 6 via glue dots. The lens group 22 further includes a tube 221 and multiple lenses 222 within the tube 221.

The optical fiber 6 adhering to the inner wall of the telescope provides a light source for the lens 21 to take pictures via an outside light source.

The circuit board 4 is a printed circuit board (PCB) or a flexible circuit board. In one embodiment, the circuit board 4 is a PCB that can provide a more stable structure and reliable performance for the telescope 1.

Figure 3:
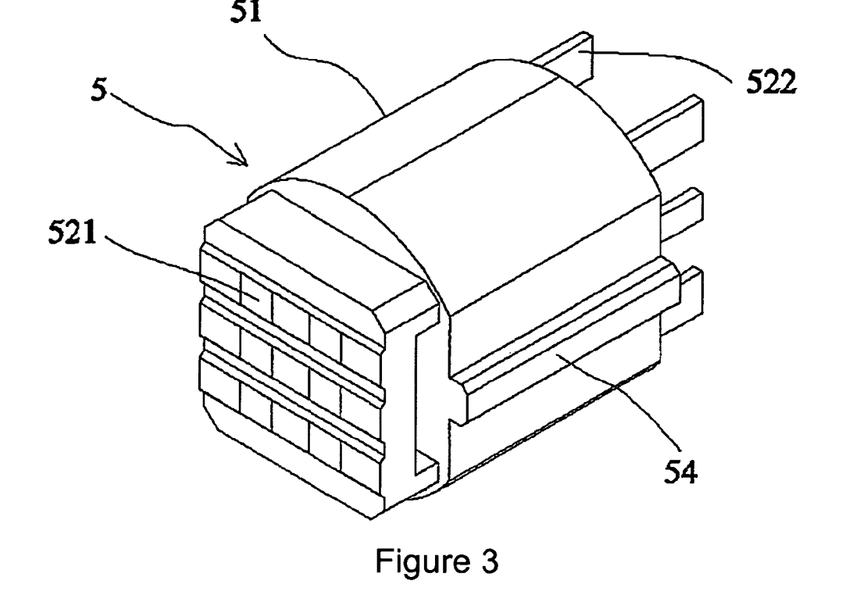
FIG. 3 is a perspective view of the connector shown in FIG. 1.
Figure 4:
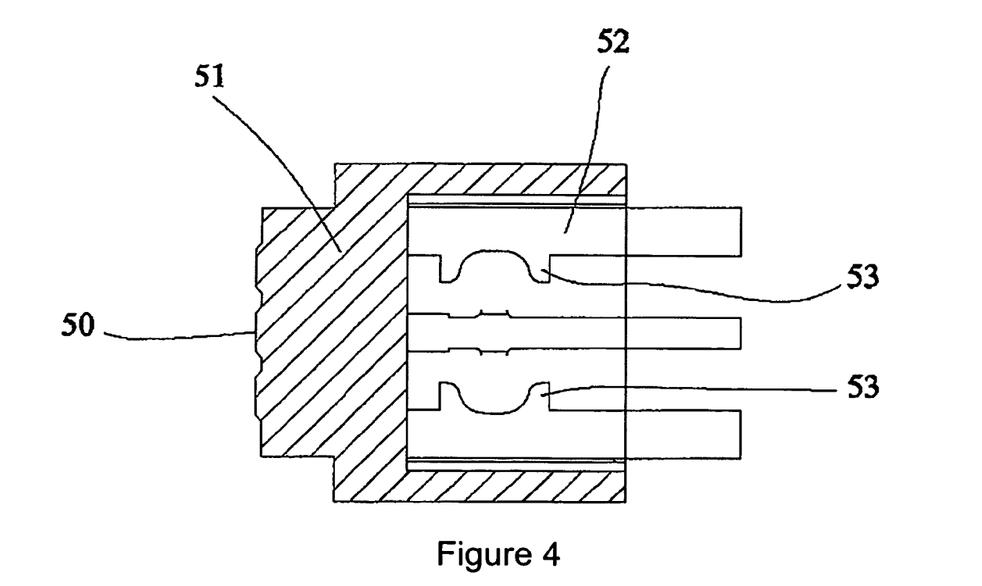
FIG. 4 is a cross-sectional view of the connector shown in FIG. 3.

As shown in FIGS. 3 and 4, the connector 5 includes a body 51 and multiple terminals 52 extending from the body 51. The body 51 is formed with the terminals 52 by insert molding. Each of the terminals 52 is electrically connected to the image sensor 3 and the circuit board 4 of the endoscope. The terminal 52 has a head portion 50 (FIG. 4) that is flat and a foot portion 522 (FIG. 3). The top surface of the head portion 50 is exposed at one end face of the body 51 to form an engagement face 521. The foot portion 522 extends from the other end face of the body 51. Multiple extending portions 53 are formed by inclining the foot portion 522 outward to provide the tight connection between the terminal 52 and the body 51.

While assembling the first assembly, the image sensor 3 and the engagement face 50 of the connector 5 are coupled together through surface mounted technology (SMT) to form an electrical connection to the head portion 50 of the terminal 52. The output end of the circuit board 4 is electrically connected to the foot portion 522 of the terminal 52.

Figure 5:
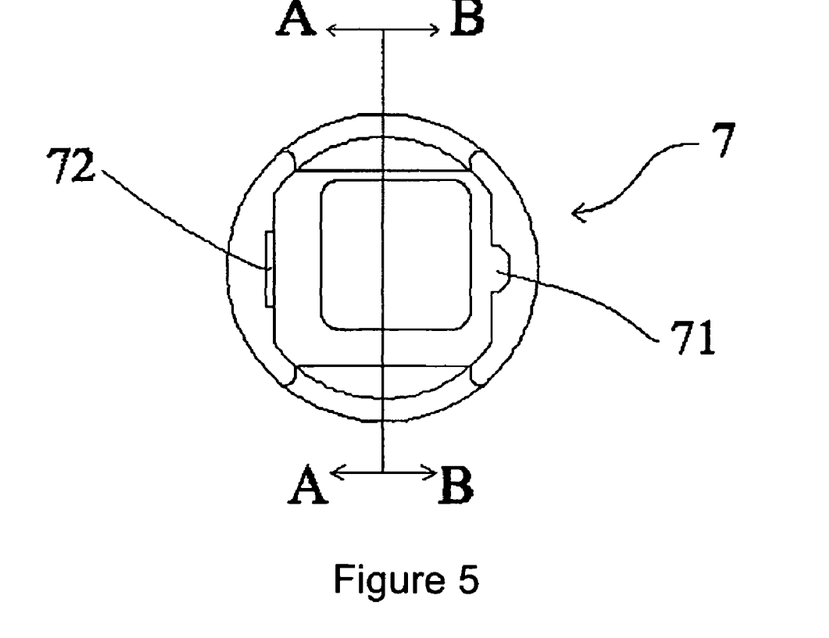
FIG. 5 is a front view of the holder shown in FIG. 1.
Figure 6:
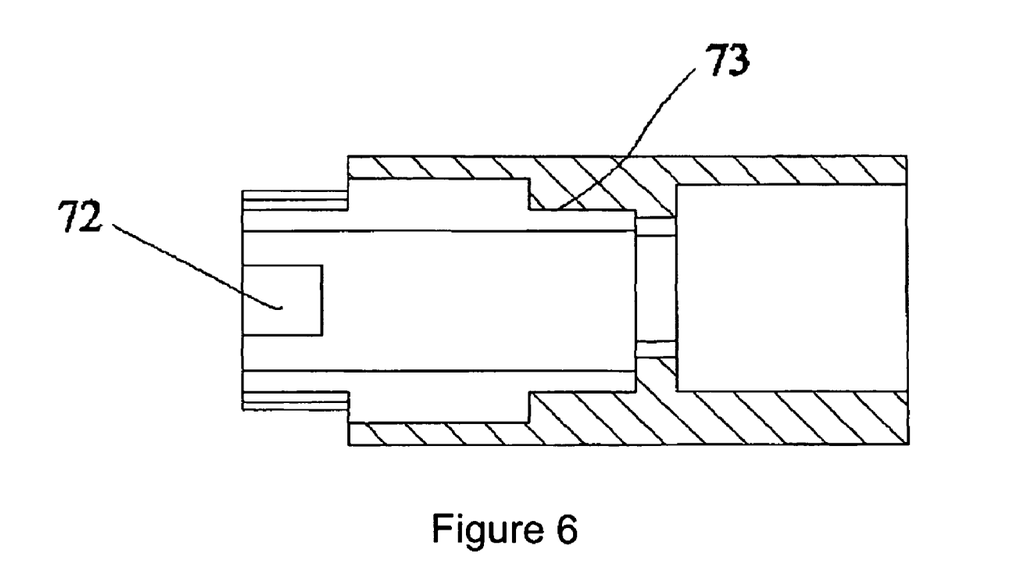
FIG. 6 is a sectional view along line A-A of FIG. 5.
Figure 7:
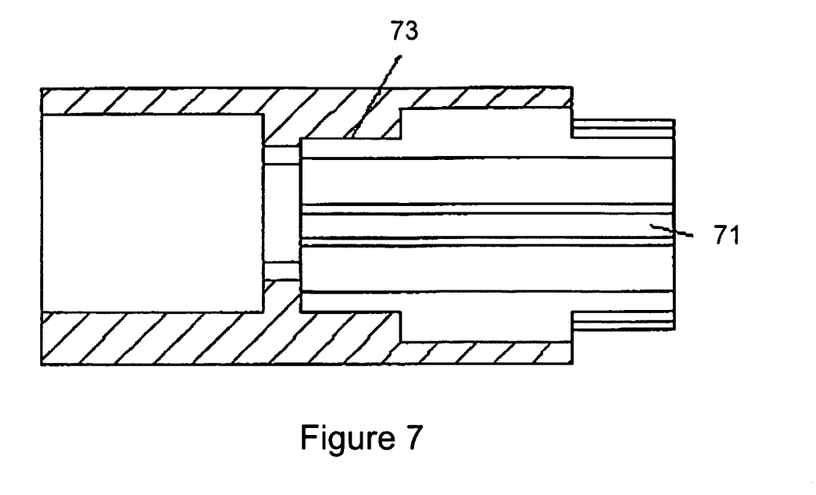
FIG. 7 is a sectional view along line B-B of FIG. 5.

In some embodiments, as shown in FIGS. 5 to 7, a holder 7 is located in the endoscope to conveniently locate and focus the imaging means 2 and the first assembly. In one embodiment, the holder 7 is located in the telescope 1 with one end connecting to the output end of the imaging means 2 to form a second assembly and the other end fixed to the first assembly. Thus the first and second assemblies are connected by the holder 7.

The holder 7 can be shaped as a tube with one end surrounding and fixed at the output end of the imaging means 2 and the other end surrounding and fixed at the connector 5. In this embodiment, one end of the holder 7 extends along the axial direction of the telescope 1 to partially surround the outer wall of the tube 221 and is fixed thereon via glue dots. There can be a focus tolerance up to 1 mm between the lens group 22 and the image sensor 3 when the optical signals are transmitted by the lens group 22. The location of the lens group 222 relative to the image sensor 3 can be axially adjusted when mounting the tube 221 to the holder 7 via glue dots to adjust the focus. In some other embodiments, the holder 7 completely surrounds the tube 221 along the axial direction of the telescope 1. In some other embodiments, the holder 7 surrounds multiple lenses 222 without using the tube 221. In this case, focus can be adjusted by adjusting the image sensor 3.

Referring to FIGS. 3, 5 and 7, a projection 54 is located at the outer side wall of the body portion 51 of the connector 5 and extends axially along the telescope 1. The projection 54 is like a bar. A corresponding groove 71 is located at the inner wall of the holder 7 to couple the projection 54. When the connector 5 is mounted onto the holder 7, the projection 54 is inserted into the groove 71. Since the image sensor 3 and the circuit board 4 have their respective orientations, the projection 54 can guide an operator to prevent the wrong orientations. Note that the locations of the projection 54 and the groove 71 can be exchanged. That is, the projection is located at the inner wall of the holder 7 and the groove is located at the outer wall of the connector 5 if there is a corresponding concave-convex structure at the connector 5 and the holder 7.

In some embodiments, a glue dot groove 72 is formed at the inner wall near the end of the holder 7 that works in concert with the connector 5 to control the glue amount used to connect the connector 5 and the holder 7. In one embodiment, there is a tolerance between the holder 7 and the connector 5 along the radial direction of the telescope 1 at the end of holder 7. By fixing the connector 5 and holder 7 using glue, the focus is achieved by radially adjusting the position of the connector 5 relative to the holder 7.

In some embodiments, the holder 7 can be as thin as 0.25 mm and a step portion 73 is formed at the inner wall of the holder 7 between the output end of the imaging means 2 and the first assembly to strengthen the holder 7.

In some embodiments, an image taken by the lens 21 is transmitted by the lens group 22 to the sensitive area of the image sensor 3, which converts the image into electrical signals and outputs the signals to the circuit board 4 for filtering. The filtered electrical signals are transmitted to another circuit board (not shown) via a digital cable 8 and are displayed on a display means (now shown).

In some embodiments, the holder 7 is made from metal powders by means of metal injection molding to achieve superior strength and precision. Metal injection molding is a formation technology that combines advantages of insert molding of plastics and powder metallurgy. Specifically, fine metal powders and macromolecular adhesive are mixed and heated to form fluid injection material. The fluid injection material is injected to form the holder 7 according to the present invention using an injection machine. The holder 7 formed herein has a more precise size and its strength is improved substantially because of metal powders. Thus the holder 7 can be made longer to locate the components in the telescope 1 more accurately.

The present invention also provides a method for manufacturing the endoscope. The method includes the steps of: connecting the image sensor 3 and the circuit board 4 via the connector 5 to form the first assembly; connecting one end of the holder 7 to the output end of the imaging means 2 to form the second assembly; connecting the other end of the holder 7 to the first assembly to integrate the first and second assemblies; adhering the optical fiber 6 to the inner wall of the telescope 1 via glue dots; and inserting the integrated first and second assemblies into the telescope 1 with the optical fiber 6 and fixing the same with glue dots. In some embodiments, the optical fiber 6 is heat-treated to withstand the heat caused by the outside light source and expansible to tightly connect the components in the telescope 1.

When connecting the imaging means 2 and the holder 7 or connecting the first assembly and the holder 7, the focus is adjusted before fixing the relative positions of the components. The focus adjustment can be done by axially adjusting the relative position between the imaging means 2 and the holder 7, by radially adjusting the relative position between the holder 7 and the first assembly, or by simultaneously adjusting the imaging means 2 and the relative position between the first assembly and the holder 7.

According to the aforementioned method, the connector 5 and the holder 7 integrate the components in the telescope 1 into one body to position them precisely, improve the image quality, and simplify the manufacturing method.

Figure 8:
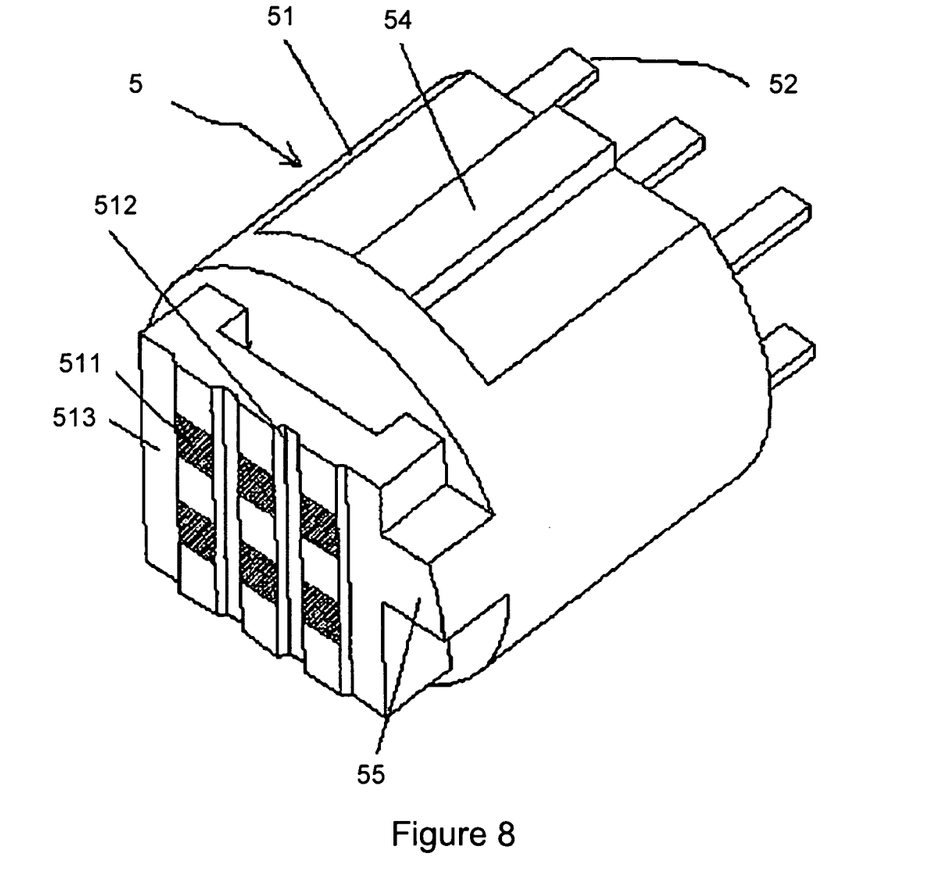
FIG. 8 is a perspective view of the connector according to another embodiment of the invention.
Figure 9:
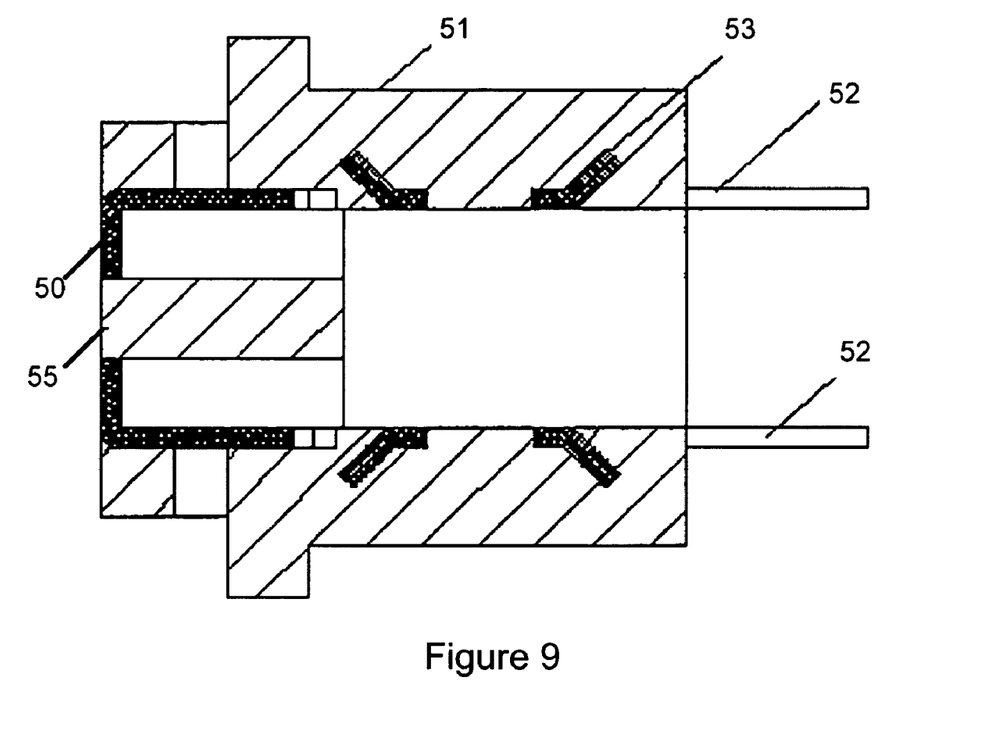
FIG. 9 is a sectional view of the connector of FIG. 8.
Figure 10:
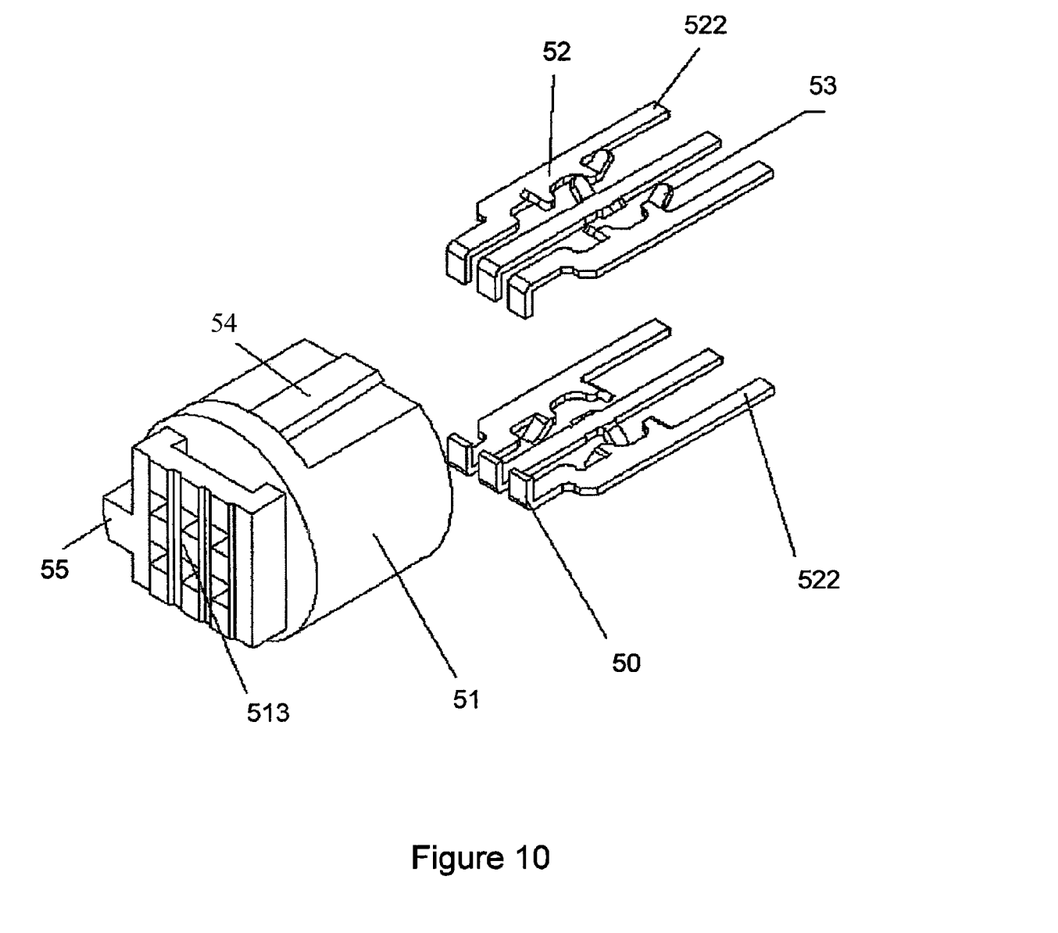
FIG. 10 is an exploded view of the connector of FIG. 8.

The present invention also discloses a connector 5. FIGS. 8 to 10 illustrate a connector according to one embodiment of the invention. As shown in FIGS. 8 to 10, the connector 5 includes a body 51 and multiple terminals 52 extending from the body 51. The body 51 is formed with the terminals 52 by insert molding. Ends of the terminals 52 are electrically connected to an image sensor 3 and a circuit board 4 of an endoscope. The terminal 52 has a head portion 50 that is flat and a foot portion 522. The top surface of the head portion 50 is exposed at one end surface of the body 51 to form an engagement face 513. The foot portion 522 extends from the other end surface of the body 51. Multiple extending portions 53 are formed by inclining the foot portion 522 outward to provide the tight connection between the terminal 52 and the body 51.

A welding pad 511 is connected to the head portion 50 and has at least one guiding groove 512 to precisely position the welding pad 511 during the insert molding.

The body 51 has a first projection 54 and a second projection 55 whose longitudinal axes are parallel to the longitudinal axes of the terminals. The projections 54 and 55 can prevent the connector from being improperly assembled onto other components.

The foot portion 522 of the terminal 52 inserts and connects to a PCB board (not shown) with the guidance of the first projection 54. The welding pad 511 of the terminal 52 can connect to a sensor (not shown) by welding with the guidance of the guiding grooves 512 and the second projection 55.

The present invention also includes a method of manufacturing the connector, which includes the following steps: pressing the material belt to form a conductive terminal; bending and extending one end of the conductive terminal to form a clamping portion; and putting at least one of the conductive terminals so obtained in position within a mould, then folding the mould and insert molding to form a connector having an insulation body and conductive terminals. In the step of pressing the material belt, two or more clamping portions having different bending directions are formed.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An endoscope, comprising:
   a telescope;
   an imaging means;
   an image sensor for converting optical images produced by the imaging means to electrical signals;
   a circuit board for receiving and outputting the electrical signals, wherein the imaging means, the image sensor and the circuit board are located in the telescope;
   a connector for electrically connecting the image sensor and the circuit board to form a first assembly; and
   a holder tube located in the telescope, wherein a first end of the holder tube is configured to surround a portion of an outer wall of the imaging means and be fixed onto the outer wall of the imaging means via glue dots, a middle section of the holder tube is configured to host the image sensor, and a second end of the holder tube is configured to surround a portion of an outer wall of the connector and be fixed onto the outer wall of the connector via a concave-convex structure such that the first assembly and the second assembly are integrated into one body.

2. The endoscope of claim 1, wherein the connector comprises a body and multiple terminals extending from the body, wherein two ends of each terminal are electrically connecting to the image sensor and the circuit board, respectively.

3. The endoscope of claim 2, wherein the terminal comprises a head portion and a foot portion, a first end of the head portion being exposed at a first end face of the body to form an engagement face and the foot portion extending out of a second end face of the body with a bent end.

4. The endoscope of claim 3, wherein the image sensor is configured to electrically connect to the engagement face of the connector and the input end of the circuit board is configured to electrically connect to the foot portions of the terminals.

5. The endoscope of claim 3, wherein multiple extending portions are formed by inclining the foot portions outward to provide a tight connection between the terminals and the body.

6. The endoscope of claim 1, wherein the concave-convex structure includes a first groove axially located at an inner wall of the holder tube and a first projection axially located at the outer wall of the connector and the first projection is inserted into the first groove to form the concave-convex structure between the holder tube and the connector.

7. The endoscope of claim 6, wherein there is a second projection transversely located at a contact surface of the connector and the second projection is inserted into a second groove axially located at the inner wall of the holder tube and there is a 90-degree rotation between the first projection and the second projection in a radial direction of the telescope to prevent misalignment between the connector and the holder tube.

8. The endoscope of claim 7, wherein the imaging means and the image sensor are respectively positioned inside the holder tube such that there is a maximum 1-mm focus tolerance between the imaging means and the image sensor in a longitudinal direction of the telescope.

9. The endoscope of claim 7, wherein a tolerance is located between the holder and the connector in a radial direction of the telescope.

10. The endoscope of claim 9, wherein a glue dispensing groove is located at the inner wall of the holder tube at an end coupling the connector.

11. The endoscope of claim 7, wherein a multi-step portion is axially located at the inner wall of the holder tube between the output end of the imaging means and the first assembly.

12. The endoscope of claim 1, wherein the imaging means includes a tube and a lens group within the tube, wherein the holder at least partially surrounds the tube along an axial direction of the telescope.

13. The endoscope of claim 1, wherein the imaging means includes a lens group and the holder tube completely surrounds the lens group.

14. The endoscope of claim 1, further comprises optical fibers located at the inner wall of the telescope to provide a light source for the imaging means.

15. The endoscope of claim 1, wherein the circuit board is a printing circuit board or a flexible circuit board.

16. A method for manufacturing the endoscope of claim 1, comprising:
   1) using the connector to electrically connect the image sensor and the circuit board to form the first assembly; and
   2) focusing the imaging means and the first assemble and fixing them within the telescope.

17. The manufacturing method of claim 16, wherein in step 2), the location of the imaging means is adjusted along the axial direction of the telescope or the location of the first assembly is adjusted along the radial direction of the telescope to adjust the focus.

18. The manufacturing method of claim 16, the method further includes locating optical fibers at the inner wall of the telescope, and after step 2) the optical fibers are heat treated to connect the components within the telescope tightly.

19. An endoscope, which comprises a telescope, an imaging means, an image sensor that converts optical signals from the imaging means into electrical signals and a circuit board that receives and outputs the electrical signals, the imaging means, image sensor and circuit board being located in the telescope, wherein the endoscope further comprises a connector that electrically connects the image sensor and the circuit board to form a first assembly, and the connector includes a body and multiple terminals passing through the body, wherein each terminal includes a head portion and a foot portion, a top surface of the head portion extends out of a first end face of the body to form an engagement face, the foot portion extends from the head portion to form a bent end out of a second end face of the body, and multiple extension portions are formed by inclining outward the foot portion to tightly connect the terminal and the body; wherein the endoscope further comprises a holder tube located in the telescope, wherein a first end of the holder tube is configured to surround a portion of an outer wall of the imaging means and be fixed onto the outer wall of the imaging means via glue dots, a middle section of the holder tube is configured to host the image sensor, and a second end of the holder tube is configured to surround a portion of an outer wall of the connector and be fixed onto the outer wall of the connector via a concave-convex structure such that the first assembly and the second assembly are integrated into one body.

* * * * *